United States Patent [19]

Bishop

[11] Patent Number: 4,747,991
[45] Date of Patent: May 31, 1988

[54] METHOD FOR DEBOSSING AND SELECTIVELY APERTURING A RESILIENT PLASTIC WEB

[75] Inventor: Delmar J. Bishop, Hamilton, Ohio

[73] Assignee: The Procter & Gamble Company, Cincinnati, Ohio

[21] Appl. No.: 486,626

[22] Filed: Apr. 20, 1983

Related U.S. Application Data

[62] Division of Ser. No. 230,919, Feb. 2, 1981, Pat. No. 4,395,215.

[51] Int. Cl.$^4$ .................. B29C 51/02; B29C 51/10; B29C 59/06

[52] U.S. Cl. ................... 264/504; 264/154; 264/284; 264/555; 428/131

[58] Field of Search ............. 264/504, 154, 284, 555; 428/131

[56] References Cited

U.S. PATENT DOCUMENTS

| | | |
|---|---|---|
| Re. 23,910 | 12/1954 | Smith et al. |
| Re. 29,524 | 1/1978 | Spencer ............................. 428/134 |
| 691,804 | 1/1902 | Parker . |
| 2,166,366 | 7/1939 | Norris ............................... 204/6 |
| 2,354,916 | 8/1944 | Hurt .................................. 264/293 |
| 2,776,452 | 1/1957 | Chavannes . |
| 2,809,392 | 10/1957 | Armstrong . |
| 2,816,025 | 12/1957 | Dahlberg ............................ 96/37 |
| 2,820,985 | 1/1958 | Cresswell . |
| 2,857,657 | 10/1958 | Wheeler, Jr. ..................... 29/156.8 |
| 2,926,490 | 3/1960 | Eaton et al. ....................... 60/35.6 |
| 2,940,125 | 6/1960 | Beucker ............................ 29/121.1 |
| 3,054,148 | 9/1962 | Zimmerli . |
| 3,123,446 | 3/1964 | Wheeler, Jr. ..................... 29/183 |
| 3,170,394 | 2/1965 | Levin ................................ 29/131 |
| 3,174,837 | 3/1965 | Mears ............................... 29/191 |
| 3,177,970 | 4/1965 | Boschi .............................. 428/137 |
| 3,312,583 | 4/1967 | Rochlis ............................. 161/62 |
| 3,390,447 | 7/1968 | Mears ............................... 29/472.3 |
| 3,489,154 | 1/1970 | Kaspar et al. .................... 428/131 |
| 3,560,601 | 2/1971 | Johnson et al. .................. 264/93 |
| 3,681,182 | 8/1972 | Kalwaites ......................... 428/131 |
| 3,814,101 | 6/1974 | Kozak ............................... 128/287 |
| 3,844,027 | 10/1974 | Hagen et al. ..................... 29/488 |
| 3,900,629 | 8/1975 | Spencer ............................ 29/163.5 R |
| 3,929,135 | 12/1975 | Thompson ........................ 128/287 |
| 3,957,414 | 5/1976 | Bussey, Jr. et al. .............. 425/384 |
| 3,979,494 | 9/1976 | Ericson ............................. 264/154 |
| 3,989,867 | 11/1976 | Sisson ............................... 428/132 |
| 4,038,040 | 7/1977 | Nagl ................................. 428/596 |
| 4,041,951 | 8/1977 | Sanford ............................. 128/287 |
| 4,091,925 | 5/1978 | Griffo et al. ..................... 428/131 |
| 4,151,240 | 4/1979 | Lucas et al. ...................... 264/504 |
| 4,155,693 | 5/1979 | Raley ................................ 264/504 |
| 4,248,822 | 2/1981 | Schmidt ............................ 264/154 |
| 4,317,792 | 3/1982 | Raley et al. ...................... 264/504 |
| 4,342,314 | 8/1982 | Radel ................................ 428/131 |

FOREIGN PATENT DOCUMENTS 2014508 8/1979 United Kingdom .
2014903 9/1979 United Kingdom .

Primary Examiner—James Lowe
Attorney, Agent, or Firm—E. Kelly Linman; John J. Ryberg; John V. Gorman

[57] ABSTRACT

Method for imparting a selectively apertured three-dimensional pattern to a heated plastic material which is either fed in film form from a supply roll or extruded as a melt directly onto the surface of a forming structure and subjected to a fluid pressure differential while in contact with its surface. In a preferred embodiment, the film forming structure comprises a stacked laminate of initially imperforate planar sheets having continuous patterns of apertures therein and at least one initially perforate selectively apertured planar sheet located beneath the uppermost continuously apertured sheet. The laminate forming structure is preferably tubular in shape so as to facilitate continuous plastic web processing against its outermost surface. Film to be debossed and selectively apertured is brought in contacting relation with the laminate structure and subjected to a substantially uniform fluid pressure differential on said forming structure while at a temperature above its softening temperature. The fluid pressure causes the heated plastic film to be debossed in those areas where said initially perforate selectively apertured lamina contacts the film and debossed and apertured in those areas where said initially perforate selectively apertured lamina does not contact the film. The debossed and selectively apertured film is thereafter cooled below its softening temperature before removal from the forming structure.

8 Claims, 9 Drawing Sheets

METHOD FOR DEBOSSING AND SELECTIVELY APERTURING A RESILIENT PLASTIC WEB

This is a division of application Ser. No. 230,919 filed Feb. 2, 1981, now U.S. Pat. No. 4,395,215 issued on July 26, 1983.

TECHNICAL FIELD

The present invention has relation to selectively apertured, resilient plastic webs exhibiting three-dimensional characteristics.

The present invention has further relation to resilient plastic webs exhibiting a substantially uniform surface texture and appearance, but which are pervious to the passage of fluids only in discrete preselected areas of the web or at preselected points along the entire surface of the web.

The present invention has further relation to method and apparatus for vacuum forming said plastic webs by uniformly heating said webs across their entire surface and applying a uniform vacuum level opposite the film-contacting surface of a forming structure of the present invention.

The present invention has still further relation to methods for constructing film forming structures suitable for debossing and selectively aperturing said plastic webs.

BACKGROUND ART

Selectively apertured sheets of material such as rubber, latex, plastic and the like have long been known in the prior art. Typical prior art structures and processes for making them are disclosed in U.S. Pat. No. 2,268,678 issued to Tingey on Jan. 6, 1942; U.S. Pat. No. 2,354,916 issued to Hurt on Aug. 1, 1944; and U.S. Pat No. Re. 23,910 issued to Smith et al. on Dec. 14, 1954. The patent to Tingey discloses a process which comprises applying a latex coagulant to a selected portion of a deposition backing, at least partially drying the coagulant, depositing a layer of latex onto the backing to at least partially coagulate a selected portion of the latex layer, and thereafter concurrently drying or gelling the remainder of the latex layer and piercing only said remainder with a plurality of fluid jets to form permanent perforations therein. The patent to Hurt discloses method and apparatus for embossing plastic sheet material wherein a perforated base may be covered with a cloth mesh which in turn may be covered with a plurality of intersecting threads to create a design. When suction is applied to the interior of the base, the plastic sheet material brought in contact therewith is caused to assume the pattern inherent in the cloth and thread design. The patent to Smith et al. discloses method and apparatus for producing textured films. In the embodiment illustrated in FIG. 4, a woven wire mesh belt has superposed thereon a specially patterned belt such that when the film being processed is subjected to vacuum it is caused to take an impression from the patterned belt.

U.S. Pat. No. 2,776,451 issued to Chavannes on Jan. 8, 1957 also discloses apparatus and method for producing embossed thermoplastic film. Chavannes discloses, in FIG. 2, a perforated vacuum forming roll covered first with wire mesh and then with fabric. Plastic film brought in contact with the surface of the drum is embossed by means of vacuum applied to the interior surface of the drum.

U.S. Pat. No. 3,054,148 issued to Zimmerli on Sept. 18, 1962 discloses a process for producing a perforated thermoplastic sheet which comprises subjecting successive portions of a continuous sheet of thermoplastic material to a uniform softening treatment, passing the softened thermoplastic material into contact with a continuously moving molding element perforated in accordance with a predetermined design, effecting selective plasticity of the sheet in contact with the molding element, subjecting a surface of the thermoplastic sheet to the action of a fluid pressure differential to cause the softened material to flow into the perforations of the molding element, maintaining the pressure differential to effect rupturing of the thermoplastic sheet in accordance with the perforations in the molding element, subjecting the soft molded thermoplastic sheet to a fixing treatment, and continuously removing the molded portions of the thermoplastic sheet from the molding element. The molding element is perforated only in those areas where it is desired to perforate the plastic sheet and is solid in those areas where no perforations are desired.

U.S. Pat. No. 3,312,583 issued to Rochlis on Apr. 4, 1967 discloses a pile-like molded product comprising a base having a plurality of parallel rows of pile formations of pyramidal shape integrally formed on and projecting from a surface thereof, the formations of the respective transversely successive rows being staggered relative to one another in the longitudinal direction of said rows, said base having apertures therethrough separating some of the pile formations of the respective rows from one another, the apertures of a given row being in transverse alignment with pile formations of an adjacent row and being overlapped longitudinally by the ends of such pile formations, the respective pile formations of said given and adjacent rows also longitudinally overlapping one another to provide an integral connection of said respective pile formations at the overlapped portions thereof. Rochlis discloses in FIGS. 21 and 22 mold cavities created by stacking laminar sheets upon one another and enclosing the ends of the cavities by assembling the laminar sheets to a base lamination. Pile-like plastic products are formed by coating the mold cavities thus produced with a softenable material, allowing the softenable material to set up, and stripping the resultant pile-like product from the mold cavity as generally shown in FIG. 19.

U.S. Pat. No. 3,966,383 issued to Bussey, Jr. et al. on June 29, 1976 discloses yet another apparatus for vacuum forming sheet thermoplastic material. The apparatus utilizes an endless, seamless structure as the forming surface. A sheet of heat softened thermoplastic film is passed over a forming screen, the forming screen being supported by a support roll, a drive roll and two seal rolls. A vacuum is applied to the screen between the seal rolls to pull the film into contact with the screen, thereby producing a three-dimensional pattern on the film corresponding to the outer surface of the screen.

Commonly assigned U.S. Pat. No. 4,151,240 issued to Lucas et al. on Apr. 24, 1979 discloses still another preferred method and apparatus for debossing and perforating a running ribbon of thermoplastic film, said patent being hereby incorporated herein by reference. Briefly, the apparatus disclosed in the Lucas et al. patent comprises means for continuously converting a ribbon of thermoplastic film into a debossed and perforated film by directing hot air jets against one surface of the film while applying vacuum adjacent the opposite surface of the film. The aforementioned operations are carried out while maintaining sufficient control of the film to substantially obviate wrinkling and/or macroscopically distending the film. In a particularly preferred embodiment, the debossing and perforating means include a rotatably mounted debossing/perforating cylinder having closed ends, a nonrotating triplex vacuum manifold assembly and hot air jet means. The film contacting surface of the debossing/perforating cylinder exhibits the pattern to be imparted to the plastic film to be treated thereon.

In a particularly preferred embodiment of the Lucas et al. invention, the debossing/perforating cylinder is constructed employing a laminate forming structure of the type generally described in the commonly assigned co-pending patent application of Clifford Radel and Hugh A. Thompson, Ser. No. 206,410, Filed Nov. 13, 1980 and entitled RESILIENT PLASTIC WEB EXHIBITING FIBER-LIKE PROPERTIES AND METHOD AND APPARATUS FOR ITS MANUFACTURE, now U.S. Pat. No. 4,342,314 on Aug. 3, 1982, said patent application being hereby incorporated herein by reference. As is pointed out in the specification of the aforesaid patent application, the laminate forming structure can be utilized to provide selective aperturing of the plastic film, particularly in areas where fluid permeability is desired, and debossing without perforating in those areas where surface texture is desired but fluid permeability is undesirable.

Even with such improved forming structures, however, prior art means for selectively aperturing plastic films have historically been dependent upon such process variables as the temperature of the film, the fluid pressure differential applied to the film and the speed of the overall operation. Thus, heating the film to a greater extent in a preselected area where aperturing is desired has typically been employed to cause rupture of the film in the preselected area when the film is subjected to a uniform fluid pressure differential while it is in contact with the forming structure. An alternative prior art practice has been to apply a greater level of vacuum to those portions of a uniformly heated plastic web to be apertured. Unfortunately, the apertured regions created in the plastic film by either technique are often poorly defined due to the difficulties associated with uniformly controlling the process variables. This is particularly true in situations where the aperturing is to be carried out in a fine pattern, is irregular in shape and/or is discontinuous in the machine direction. Furthermore, such prior art techniques are impractical where it is desired to impart a uniform surface texture and appearance along the entire surface of the web with fluid permeability only at preselected points along the entire surface of the web.

A further difficulty inherent in such prior art processes is that aperturing of the film often results even where it is undesired, particularly where large, relatively weak, unsupported areas are to be debossed by the application of fluid pressure thereto.

Accordingly, it is an object of the present invention to provide method and apparatus for accurately debossing and selectively aperturing a uniformly heated plastic web in nearly any desired predetermined pattern by subjecting the entire surface of said web to a uniform fluid pressure differential on a forming structure of the present invention.

It is another object of the present invention to provide feasible methods for constructing three-dimensional forming structures for imparting a selectively apertured three-dimensional pattern to a heated plastic film which is subjected to a fluid pressure differential while in surface contact therewith.

It is yet another object of the present invention to provide a three-dimensional plastic film precisely apertured only at predetermined points or in predetermined areas, said web exhibiting a substantially uniform overall surface texture and appearance in both the apertured and non-apertured areas thereof.

DISCLOSURE OF THE PRESENT INVENTION

The present invention pertains, in a particularly preferred embodiment, to the provision of a three-dimensional resilient plastic web exhibiting a uniform surface texture and appearance across its entire width, but which is rendered fluid pervious only at predetermined points or in predetermined areas. The portions of the film to be apertured are determined by the character of the forming structure on which it is subjected to a substantially uniform fluid pressure differential.

In yet another embodiment of the present invention, a method for constructing a three-dimensional film forming structure for imparting a selectively apertured three-dimensional pattern to a heated plastic film which is subjected to a fluid pressure differential while in contact with its surface is provided, said method preferably comprising the steps of:

(1) forming substantially continuous patterns of apertures in a multiplicity of initially imperforate planar sheets, at least a portion of said sheets having aperture patterns which are similar to one another;

(2) forming a pattern of aperture corresponding to the portions of said film to be selectively apertured in an initially perforate planar sheet, said pattern of apertures substantially coinciding with the pattern of apertures in at least one of said initially imperforate planar sheets;

(3) superposing said initially imperforate apertured planar sheets and said initially perforate, selectively apertured planar sheet upon one another so that said initially perforate, partially apertured planar sheet is located below the uppermost sheet and adjacent at least one of said initially imperforate, apertured sheets having a pattern of apertures substantially coinciding with the apertured portion of said initially perforate, partially apertured sheet; and (4) bonding said superposed stack of sheets to one another at contact points to form an integral laminate film forming structure.

In a particularly preferred embodiment of the present invention, the uppermost surface of the aforementioned laminate structure is caused to assume a radius of curvature greater than that of the lowermost surface of said laminate structure without causing delamination thereof, as by mechanical rolling. This causes the laminate structure to assume a substantially tubular shape. In the latter embodiment, the opposing free edges of said tubular-shaped laminate structure are secured to one another while maintaining substantial continuity of the three-dimensional, selectively apertured pattern exhibited by said laminate structure about its entire periphery.

The laminate tubular member permits continuous web processing. It is preferably utilized in a vacuum forming operation which is conducted in concert with a curtain of hot air which flash heats either a plastic film or an extruded plastic melt sufficiently to effect substantial conformance to the three-dimensional pattern embodied in the tubular member when vacuum is applied to the interior surface thereof. Thus debossing occurs across the entire surface of the plastic web, while debossing and aperturing takes place only in those areas where the apertures in said initially perforate planar sheet coincide with the pattern of apertures in one of the initially imperforate apertured sheets in the remainder of the laminate film forming structure. The support provided to the film by the non-coinciding portions of the initially perforate, partially apertured sheet prevents rupturing of the film at the fluid pressures required to perforate the unsupported portions of the film. Thus, in the practice of the present invention, a uniform level of vacuum may be employed across the entire surface of the tubular-shaped forming drum, and the temperature of the plastic web may be substantially uniform across its entire surface during the processing operation. Unlike prior art techniques employing non-uniform fluid pressures and/or non-uniform web temperatures, precisely defined aperturing of a web of plastic film in accordance with the present invention is controlled primarily by the character of the novel forming structure rather than by process variables.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE PRESENT INVENTION

While the present invention will be described in the context of providing a uniformly textured, but selectively apertured top sheet on an absorbent bandage such as a disposable diaper, the present invention is in no way limited to such application. To the contrary, the present invention may be practiced to great advantage in many situations where it is desired to produce a plastic film or web exhibiting a uniform three-dimensional pattern across its entire surface, but which is pervious to the passage of fluid and/or gas only at predetermined points along the entire surface of the web or in certain preselected areas of the web. The pattern of apertures created may be of any desired shape, they may be regulated or random, reticulated or nonreticulated, continuous or interrupted, or any desired combination thereof. The detailed description of the preferred structure and its use as a top sheet in a disposable diaper will allow one skilled in the art to readily adapt the invention to other devices.

Figure 1:
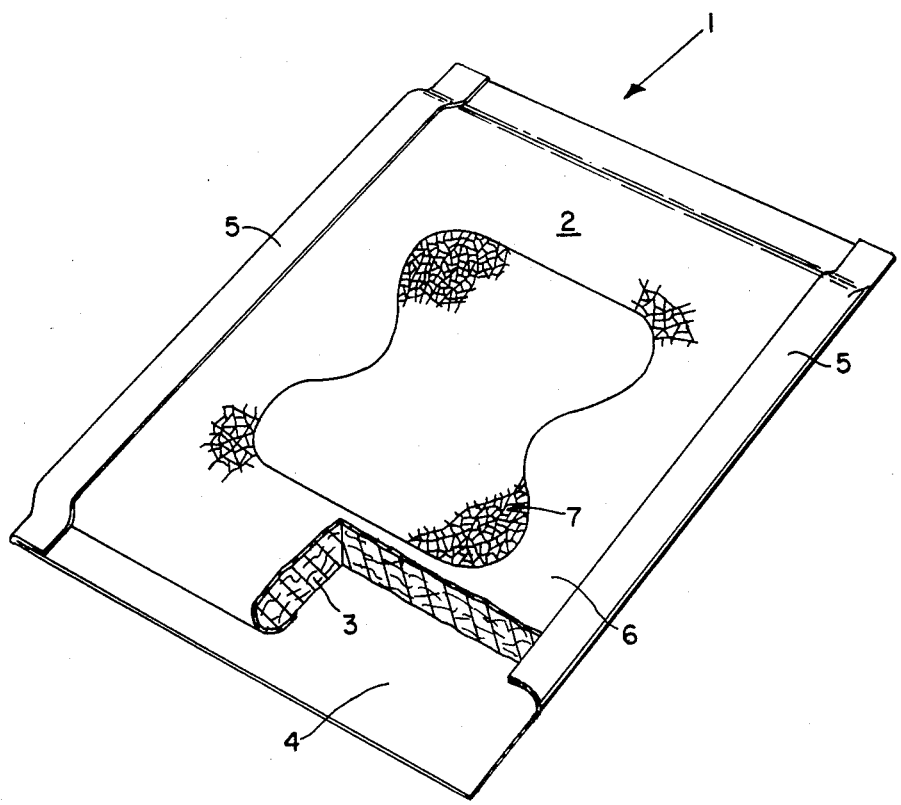
FIG. 1 is a simplified perspective representation of an unfolded disposable diaper with portions of its components cut away.

FIG. 1 is a perspective view of a disposable diaper in an unfolded condition. Various layers have been cut away to more clearly reveal the structural details of this embodiment. The disposable diaper is referred to generally by the reference numeral 1. The top sheet is shown at 2. The other two major components of the disposable diaper 1 are the absorbent element or pad 3 and the back sheet 4, which is preferably resistant to the passage of absorbed fluids. In general the side flaps 5 of the back sheet 4 are folded so as to cover the edges of the absorbent pad 3 and top sheet 2. Top sheet 2 is generally folded to completely enclose the ends of the absorbent pad 3. The drawing of diaper 1 in FIG. 1 is a simplified representation of a disposable diaper. A more detailed description of a preferred embodiment of a disposable diaper is contained in U.S. Pat. No. 3,952,745 issued to Duncan on Apr. 27, 1976, said patent being hereby incorporated herein by reference.

The illustrated diaper embodiment 1 shown in FIG. 1 employs a selectively apertured plastic top sheet 2 which, when viewed by the user, exhibits a substantially uniform three-dimensional surface texture and feel across its entire surface. However, the top sheet 2 has been selectively apertured so as to be fluid-pervious only in the area generally designated as 7, while those portions of the top sheet generally designated as 6 remain imperforate and consequently impervious to the passage of fluid. Since the points of fluid entry are reasonably well defined in absorbent bandages such as disposable diapers, sanitary napkins, incontinent pads and the like, selective aperturing of the top sheet only in those areas which are subject to the discharge of body fluids permits the discharged fluids to readily pass through the apertured portions of the top sheet and be absorbed within the absorbent element or pad 3.

Because the imperforate portions 6 of the top sheet 2 are impervious to the passage of fluids they completely prevent reverse flow of the absorbed fluids back to the surface of the top sheet in contact with the wearer, even when subjected to pressure caused by movements of the wearer. This provides more effective containment of the absorbed fluids as well as greater overall film strength in those areas where fluid permeability is not essential.

Because the disposable diaper 1 is less subject to rewet of its wearer contacting surface due to the limited size of the fluid pervious portion 7 of the top sheet 2, the structure can be worn for longer periods to more effectively utilize the absorbent capacity of the absorbent element 3 without causing any increase in wearer discomfort due to surface wetness of the top sheet 2 in the imperforate areas 6. Because the absorbent element 3 is constrained between the plastic top sheet 2 which is fluid-pervious only in area 7 and back sheet 4 which is also resistant to the passage of absorbed fluids, the absorbed fluids are substantially prevented from escaping along the periphery of the absorbent pad element 3, thereby preventing wetting of garments coming in contact with the edges of the diaper 1.

A further advantage of a selectively apertured top sheet 2 of the type generally disclosed in FIG. 1 is that it permits ready absorption of body fluids having an unpleasant appearance and thereafter masks the absorbed fluids from the user's view by means of the imperforate portions 6 surrounding the selectively apertured area 7. Thus the user is able to fully utilize the absorbent capacity of the absorbent element 3 without encountering the unsightly appearance typically exhibited by absorbent structures having their entire top sheets pervious to the passage of fluids. This factor is of particular significance where personal care products such as sanitary napkins, surgical drapes, wound bandages, and the like are employed to transmit or absorb highly visible body exudates.

Selective aperturing in accordance with the present invention is not, however, limited to the provision of three-dimensional plastic webs having predetermined areas which are pervious to fluids, including gases. It may be applied to even greater advantage in situations where limited fluid permeability is desired along the entire surface of the web, e.g., in situations where the points of fluid transfer, whether in liquid or gaseous form, are not well defined. One illustrative use of a three-dimensional film exhibiting limited fluid permeability over its entire surface might be as a breatheable back sheet for a disposable diaper. In such a situation, a three-dimensional debossed pattern may be applied to improve the visual and tactile impression of the entire back sheet while selective aperturing may be employed to provide limited fluid permeability along the entire surface of the back sheet. By proper design, such a back sheet can be made to permit vapor transfer therethrough yet avoid fluid leakage.

As has been pointed out earlier herein, means for debossing and selectively aperturing moving plastic webs are well known in the art. Typically, these prior art means involve applying a greater fluid pressure differential, most typically vacuum, to those portions of the web to be apertured while said web is at a substantially uniform elevated temperature and in contact with a forming structure. Alternatively, the plastic film may be selectively heated to a greater extent in those areas where apertures are desired, such that the film is more prone to rupture in the elevated temperature areas when subjected to a substantially uniform fluid pressure differential on a forming structure. If desired, non-uniform heating of the plastic web and the application of non-uniform fluid pressures to the web may be used in conjunction with one another. However, it has generally been found that the greater the number of process variables to be controlled, the greater will be the difficulty in producing consistent results in the film. Furthermore, such prior art selective aperturing techniques are not practical where only predetermined points along the entire surface of the web are to be made fluid pervious.

Figure 2:
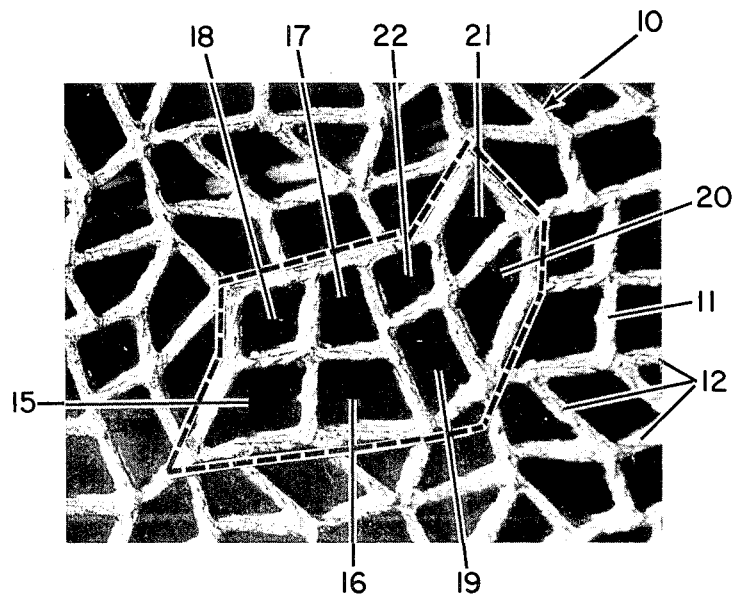
FIG. 2 is a plan view photograph enlarged approximately twelve times actual size of the film contacting surface of a laminate film forming structure of the type generally disclosed in the commonly assigned co-pending patent application of Clifford Radel and Hugh A. Thompson, Ser. No. 206,410, filed Nov. 13, 1980 and entitled RESILIENT PLASTIC WEB EXHIBITING FIBER-LIKE PROPERTIES AND METHOD AND APPARATUS FOR ITS MANUFACTURE, now U.S. Pat. No. 4,342,314 issued on Aug. 3, 1982, said structure being comprised of a multiplicity of initially imperforate planar sheets having similar aperture patterns therein.

FIG. 2 is a plan view photograph enlarged approximately twelve times actual size of a laminate forming structure made generally in accordance with the teachings of the co-pending, commonly assigned patent application of Clifford Radel and Hugh A. Thompson, Ser. No. 206,410, filed Nov. 13, 1980 and entitled RESILIENT PLASTIC WEB EXHIBITING FIBER-LIKE PROPERTIES AND METHOD AND APPARATUS FOR ITS MANUFACTURE, now U.S. Pat. No. 4,342,314 issued on Aug. 3, 1982, said patent application being hereby incorporated herein by reference. Briefly, the laminate forming structure 10 was formed generally in accordance with the teachings of said patent application by photoetching six identically patterned stainless steel sheets, each sheet having a thickness of about five mils, copper plating the exterior surfaces of the individual stainless steel sheets with a coating approximately 0.1 mils thick, and thereafter furnace brazing the sheets to one another at a temperature of about 2,050° F. while said sheets were secured in a stacked condition so that their aperture patterns are aligned in superposed relation with one another to form a fine scale perforate forming surface exhibiting a multiplicity of irregularly shaped apertures, i.e., 15, 16, 17, 18, 19, 20, 21, 22, etc.

The uppermost surface 11 of the laminate forming structure 10 exhibits a plurality of striations 12 across its entire surface to provide surface imperfections which tend to minimize any resultant gloss in plastic films subjected to a forming operation thereon. This is preferably accomplished by striating the resist coating on the uppermost lamina during the photoetching process, as generally disclosed in the aforementioned patent application of Radel et al.

Figure 3:
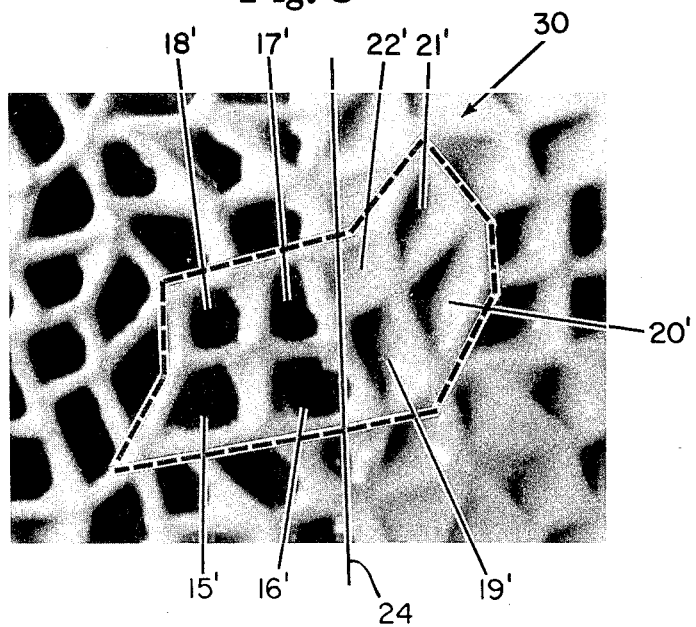
FIG. 3 is a plan view photograph enlarged approximately twelve times actual size of a plastic film which has been caused to conform to a forming structure of the type generally illustrated in FIG. 2, the apertured portions of the film having been created by the application of a higher level of vacuum to the non-film contacting surface of the laminate structure.

In FIG. 3 there is shown a selectively apertured 1.4 mil thick polyethylene plastic film 30 which has been simultaneously subjected to two different levels of fluid pressure, i.e., vacuum, while in contact with a laminate forming structure 10 of the type generally illustrated in FIG. 2. The condition of the film 30 is shown in FIG. 3 prior to removal from the forming structure 10.

The film illustrated in FIG. 3 was produced by uniformly heating the film across its entire surface to a temperature of approximately 400° F. Those portions of the film to the left of dividing line 24, which defines the approximate line of separation between the apertured and non-apertured portions of the film, were subjected to a vacuum of approximately 17 inches of mercury applied to the lowermost surface of the forming structure 10, while those portions to the right of dividing line 24 were subjected to a vacuum level of approximately 4 inches of mercury. The lower level of vacuum applied to the righthand portions of the heated web was sufficient to cause substantial conformance between the plastic film 30 and the forming structure 10, yet insufficient to cause wide scale aperturing of the film in the irregularly shaped debossed areas of which 19', 20', 21' and 22' are typical. As will be apparent from a comparison of FIGS. 2 and 3, the pattern formed by debossed areas 19' through 22' in the film 30 corresponds to the pattern formed by apertures 19 through 22, respectively, in forming structure 10. Conversely, the higher vacuum level applied to that portion of film 30 to the left of dividing line 24 was sufficient to cause not only debossing but also rupturing of the film to form apertures of which 15', 16', 17' and 18' are typical. As with the non apertured portions of the film 30, the pattern formed by apertures 15' through 18' in the film 30 corresponds to the pattern formed by apertures 15 through 18, respectively, in forming structure 10.

Figure 4:
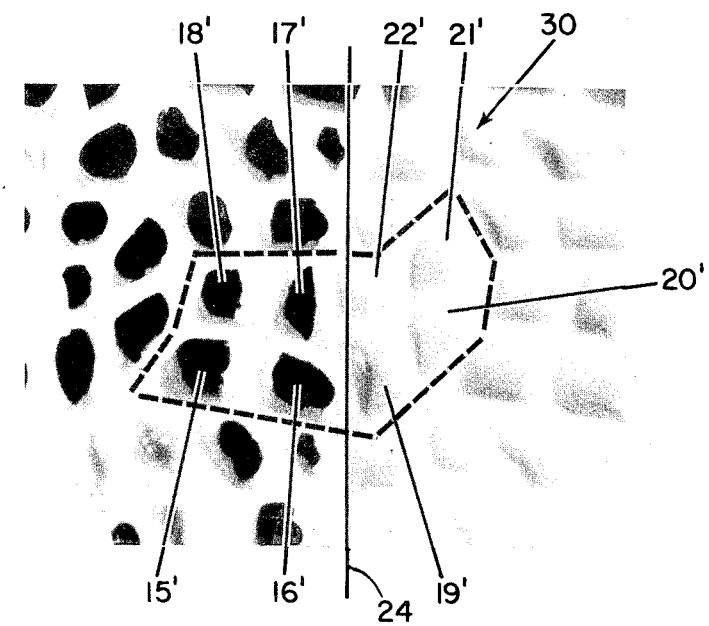
FIG. 4 is a plan view photograph enlarged approximately twelve times actual size of a selectively apertured plastic film of the type shown in FIG. 3 after removal from the laminate forming structure.

FIG. 4 is a plan view photograph enlarged approximately twelve times actual size of a selectively apertured plastic film 30 of the type generally illustrated in FIG. 3 after removal from the laminate forming structure 10.

Figure 5:
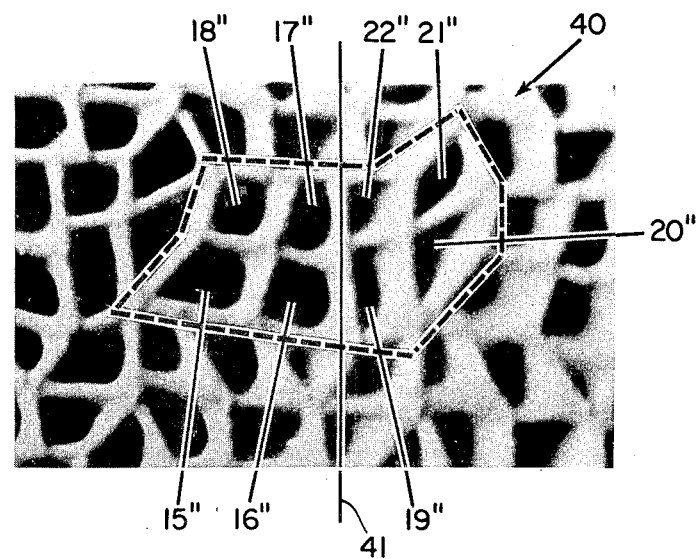
FIG. 5 is a plan view photograph enlarged approximately twelve times actual size of a plastic film which has been caused to conform to a laminate forming structure of the type generally illustrated in FIG. 2, said film having been selectively apertured by elevating the temperature of the film in the areas where fluid permeability is desired and applying a uniform level of vacuum to the non-film contacting surface of the laminate structure.

FIG. 5 is a plan view photograph enlarged approximately twelve times actual size of an alternative selectively apertured 1.4 mil thick polyethylene plastic film 40 also formed by applying a fluid pressure differential to the film while in contact with a forming structure of the type generally illustrated in FIG. 2. In FIG. 5 the film 40 is shown in contact with the forming structure. The imperforate portions of the film to the right of dividing line 41 were elevated to a temperature of approximately 300° F. while the apertured portions of the film to the left of dividing line 41 were elevated to a temperature of approximately 750° F. A vacuum level of about 6 inches of mercury was applied to the entire lowermost surface of the forming structure 10 while the heated film was in contact therewith.

As can be seen in FIG. 5, the higher temperature of those portions of the film 40 to the left of dividing line 41 sufficiently weakened the film to allow rupture and formation of fluid-pervious apertures such as 15", 16", 17" and 18" therein. Those portions of the film 40 to the right of dividing line 41 were caused to conform to the laminate forming structure 10, but due to the lower temperature of the film, fluid-impervious debossed areas such as 19", 20", 21" and 22" were created instead of apertures. A comparison of FIGS. 5 and 2 reveals the pattern correspondence between film apertures 15" through 18" and forming structure apertures 15 through 18, respectively, as well as between debossed areas 19" through 22" and forming structure apertures 19 through 22, respectively.

Figure 6:
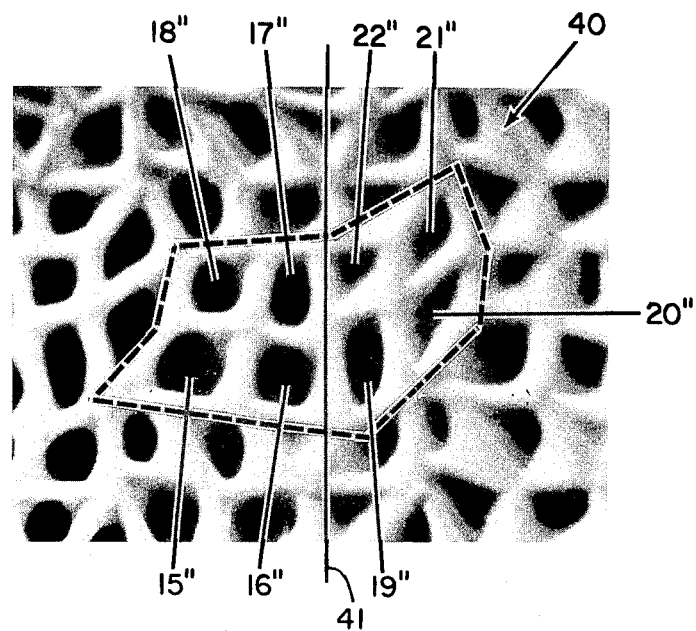
FIG. 6 is a plan view photograph enlarged approximately twelve times actual size of a selectively apertured plastic film of the type illustrated in FIG. 5 after removal from the laminate forming structure.

FIG. 6 is a plan view photograph enlarged approximately twelve times actual size of a selectively apertured plastic film 40 of the type generally shown in FIG. 5 after removal from a laminate forming structure of the type generally illustrated in FIG. 2. As can be seen from FIG. 6, separation between the apertured and non-apertured portions of the film 40 is approximately along dividing line 41, which substantially coincides with the line along which differential temperatures were applied during processing.

Figure 7:
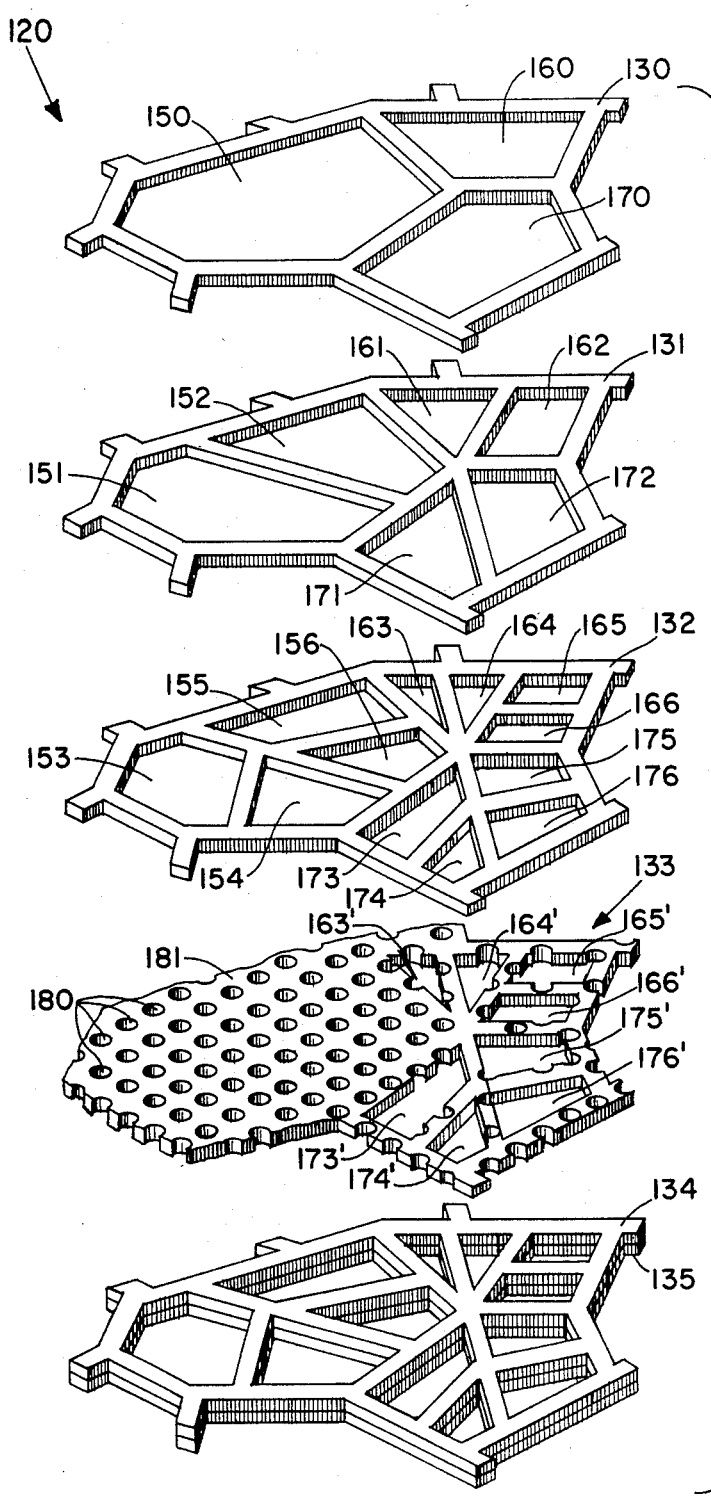
FIG. 7 is an enlarged, partially exploded, perspective view of a laminate forming structure of the present invention, the laminae in the uppermost portions of said structure being exploded for clarity.

FIG. 7 is a simplified, partially exploded, perspective illustration of a particularly preferred photoetched laminate forming structure 120 of the present invention. The laminate structure 120, which is preferably constructed generally in accordance with the teachings of the aforementioned co-pending, commonly assigned patent application of Clifford Radel and Hugh A. Thompson, is comprised of a stack of individual sheets or laminae 130, 131, 132, 133, 134 and 135. Each lamina has a pattern of openings or apertures therein. The laminae may be made from any suitable material capable of being apertured and bonded. Stainless steel is particularly preferred where the laminae are to be apertured by photoetching and bonded by copper plating and furnace brazing.

As will be apparent from FIG. 7, laminae 132, 134 and 135 are identical to one another. If desired, all laminae in a given forming structure may employ an identical pattern of apertures. This is the case with the forming structure embodiment 10 illustrated in FIG. 2. However, if a network of decreasing capillary size is desired, it is necessary to employ coinciding apertures of decreasing size in successive laminae or to further subdivide the aperture patterns in the direction of the lowermost surface of the structure. In the latter case, which is illustrated in FIG. 7, it is typical to employ several identical laminae superposed upon one another to provide sufficient depth of pattern in each dissimilar portion of the laminate structure. However, for simplicity of illustration a single uppermost lamina 130 and a single intermediate lamina 131 are shown. Lamina 130 exhibits a patterned arrangement of irregular openings 150, 160, 170 which when superposed on lamina 131 align generally with the peripheral border formed by each pair of openings 151, 152; 161, 162; and 171, 172, respectively. Similarly, the peripheral borders formed by each group of openings 153, 154, 155 and 156; 163, 164, 165 and 166; and 173, 174, 175 and 176 in lamina 132 are generally aligned with the peripheral border formed by openings 151, 152; 161, 162; and 171, 172, respectively, in lamina 131. From the foregoing descriptions, it is readily apparent how intricate three-dimensional geometric structures exhibiting a continuous capillary network of decreasing size in the direction of the lowermost surface of the structure can be created. Utilizing the technique set forth in detail in the aforementioned co-pending commonly assigned patent application of Radel et al., nearly any three-dimensional pattern which is desired may be created.

As will be apparent from an inspection of FIG. 7, laminae 130, 131, 132, 134 and 135 are formed from a planar sheet which is initially imperforate in accordance with the teachings of the aforementioned application of Radel et al. For ease of fabrication lamina 133 may, if desired, be formed from a planar sheet initially containing a closely spaced pattern of small perforations 180. Alternatively, the pattern of perforations 180 may be formed simultaneously with the pattern of coinciding apertures 163', 164', 165', 166', 173', 174', 175', 176', etc.

To provide support to the film or melt being processed on a forming structure of the present invention, the perforations 180 must be generally smaller in size than the apertures to be produced in the film. Experience with perforations and film apertures having a maximum to minimum dimension ratio in the neighborhood of 1:1, respectively, has shown that unwanted rupturing of the film may normally be avoided when the maximum dimension of the individual perforation, e.g., the diameter of perforation 180, in lamina 133, is not more than about 25 percent of the maximum dimension of the smallest aperture to be formed in the resultant film, e.g., the maximum dimension of the film aperture corresponding to opening 174' in lamina 133.

Spacing of the individual perforations, such as 180, must be sufficiently frequent that conformance of the film to the forming structure will be achieved when suction is applied to the lowermost surface thereof. Accordingly, the particular pattern of perforations to be employed in those portions of lamina 133 used to form the debossed, non-apertured areas of the film will depend upon the complexity, size and depth of the debossed areas desired in the resultant film.

In the illustrated embodiment, lamina 133 is preferably photoetched with a pattern of apertures 163', 164', 165', 166', 173', 174', 175' and 176' corresponding to apertures 163, 164, 165, 166, 173, 174, 175 and 176, respectively in lamina 132. These are the areas in which aperturing of the plastic film is desired. Where debossing of the plastic film without aperturing is desired, the sheet from which lamina 133 is formed, which in a particularly preferred embodiment is initially perforate, is not photoetched to coincide with the pattern of apertures present in the adjacent lamina, e.g., apertures 153, 154, 155 and 156 in lamina 132.

In an alternative embodiment lamina 133 may be constructed from more than a single sheet by splicing a lamina such as 132 with a sheet of perforate material such as the non-apertured portion 181 of lamina 133 in butt joint fashion along any desired line of demarcation between the areas of the film to be debossed only and the areas to be debossed and apertured.

Where the individual laminae are very thin, it may also be feasible to completely remove the areas to be apertured from lamina 133 along their peripheral borders and leave the adjacent laminae, in the illustrated case 132, 134, unsupported by lamina 133 in said areas. This particular method was employed in constructing laminate forming structure 210 illustrated in FIG. 8.

In still another embodiment, a selectively apertured lamina such as 133 could be employed as the lowermost member of the laminate stack. In such case, those portions of lamina 133 corresponding to the pattern in the resultant film would be removed from the lamina. By maintaining the selectively apertured lamina 133 independent from the balance of the laminate structure, the pattern of selective aperturing to be imparted to the film could be changed merely by changing the selectively apertured lamina.

Practice of the present invention offers a further advantage over prior art techniques where debossing of the plastic film to different depths is desired. In such a situation, a selectively apertured, lamina may be incorporated at more than one level within the forming structure to provide multiple levels of debossing and selective aperturing in the resultant film.

Regardless of the particular fabrication method chosen for constructing the selectively apertured lamina 133 illustrated in FIG. 7, the resultant laminate film forming structure 120 is preferably subjected to a uniform fluid pressure differential while an initially imperforate web of plastic film of substantially uniform temperature is in contact with its uppermost surface. As has been pointed out earlier herein, said web may be fed in film form from a supply roll, or extruded as a melt directly onto a forming structure of the present invention. Regardless of which form of plastic introduction is employed, the fluid pressure differential causes the heated film to conform thereto along its entire surface. Because of the support provided to the film by the unetched perforate portion 181 of lamina 133, the film is caused to conform to the laminate forming structure 120 without rupturing. However, in those areas of the forming structure 120 wherein lamina 133 exhibits coinciding apertures 163', 164', 165', 166', 173', 174', 175' and 176', debossing and rupturing of the film in accordance with said pattern of apertures occurs.

Vertical or z-direction placement of a selectively apertured lamina, e.g., lamina 133, in a laminate forming structure of the present invention controls the depth of draw in film processed thereon. However, improper z-direction placement can also cause unwanted aperturing of the film to take place. If the selectively apertured lamina is placed too great a distance from the uppermost surface of the lamina, the film will be unable to obtain any support prior to rupturing. On the other hand, if a selectively apertured lamina is placed too near the uppermost surface of the laminate forming structure, the depth of deboss in the resulting film may be insufficient to produce a uniform appearance across both the apertured and nonapertured areas of the web. The particular z-direction placement of the selectively apertured lamina is dependent upon a number of variables which must be taken into consideration in order to obtain the desired results. Several of the more important factors are:

(a) the rheological properties of the base plastic material to be processed;
(b) the temperature of the plastic material at the deformation stage;
(c) the rate of deformation;
(d) the size and geometry of the apertured and non-apertured deformations to be produced in the web; and
(e) the temperature of the laminate forming structure.

The rheological properties of the plastic material which are of primary interest in the present context are the "relaxation time" of the material, as generally described at pages 90–95 of the 1971 edition of *Mechanical Properties of Solid Polymers*, I. M. Ward, John Wiley & Sons, New York, and the "elongational viscosity" of the material, as generally described at pages 184–190 of the 1979 edition of *Principles of Polymer Processing*, Z Tadmer and C. Gogos, John Wiley & Sons, New York, said references being hereby incorporated herein by reference. The relaxation time is a characteristic time constant for the decay of stress with time in a material, while the elongational viscosity is a measure of the resistance of a material to rate of deformation under pure normal stress. In general, experience has shown that for materials having shorter relaxation times and lower elongational viscosities, a greater draw of the material is possible prior to rupture. Thus, Z-direction placement depth of the selectively apertured lamina may generally be increased for such materials.

As the temperature of the plastic material and the laminate forming structure are increased, it has generally been found easier to draw the material without rupture. Accordingly increased temperatures generally permit greater Z-direction placement depths for the selectively apertured lamina.

Conversely, the greater the rate of plastic deformation the more difficult it is to draw the material without rupture. Therefore, shallower Z-direction placement depths are generally preferred as formation rates are increased.

Finally, the size and geometry of the particular deformation will greatly affect Z-direction placement depth for the selectively apertured lamina. For apertures having length to width ratios approaching unity, the larger the size of the aperture, the shallower should be the depth of placement. Similarly, the more tortuous and irregular the geometry, the shallower should be the depth of placement.

It will of course be recognized by those skilled in the art that these criteria must be considered on a case by case basis to arrive at optimum Z-direction placement of the selectively apertured lamina for any particular situation.

Since the draw depth of the film can be controlled by appropriate Z-direction placement of selectively apertured lamina 133, as described earlier herein, selective aperturing of the plastic film at predetermined points or in predetermined areas may likewise be precisely controlled without the need to apply differing levels of fluid pressure to the lowermost surface of the forming structure and without the need to heat the film to differing temperature levels across its surface. Accordingly, the present invention permits overall three-dimensional texturing of a moving plastic web in combination with selective aperturing of predetermined points or areas of said web. The apertured points or areas may be of any desired shape, isolated or non-isolated from one another and continuous or discontinuous in the direction of web processing. As will be appreciated by those skilled in the art, these objectives are extremely difficult, if not impossible, to achieve by prior art variable vacuum and variable temperature techniques.

In addition to the foregoing advantages, it should be noted that practice of the present invention offers another benefit not provided by prior art selective aperturing techniques. Namely, in situations where individual non-apertured debossments which are very large in size are desired, it is extremely difficult to completely deboss the plastic material without causing rupture thereof. This is due to the lack of film support across the large discrete areas to be debossed. Employing a lamina exhibiting a fine scale pattern of perforations, e.g., perforations 180 in portion 181 of lamina 133, in a laminate forming structure of the present invention provides localized support to the film during the debossing operation. Such a lamina, which in a particularly preferred embodiment is selectively apertured, permits effectively debossing the film to nearly any desired depth in patterns employing very large debossments without causing undesired rupture thereof.

While proper Z-direction placement of the selectively apertured lamina, e.g., lamina 133, is necessary to effectively control aperturing of the film, it should be noted that it is also preferable in the practice of the present invention to prevent the portions of the film which are apertured from wrapping about the lowermost surface of the forming structure upon rupture. This avoids mechanical locking of the film to the forming structure, thereby making removal of the film from the forming structure relatively easy. In a particularly preferred embodiment of the present invention this may be accomplished by providing additional laminae, e.g., laminae 134 and 135, below the selectively apertured lamina. These additional laminae prevent the ruptured portions of the film from reaching the lowermost surface of the laminate forming structure.

Figure 8:
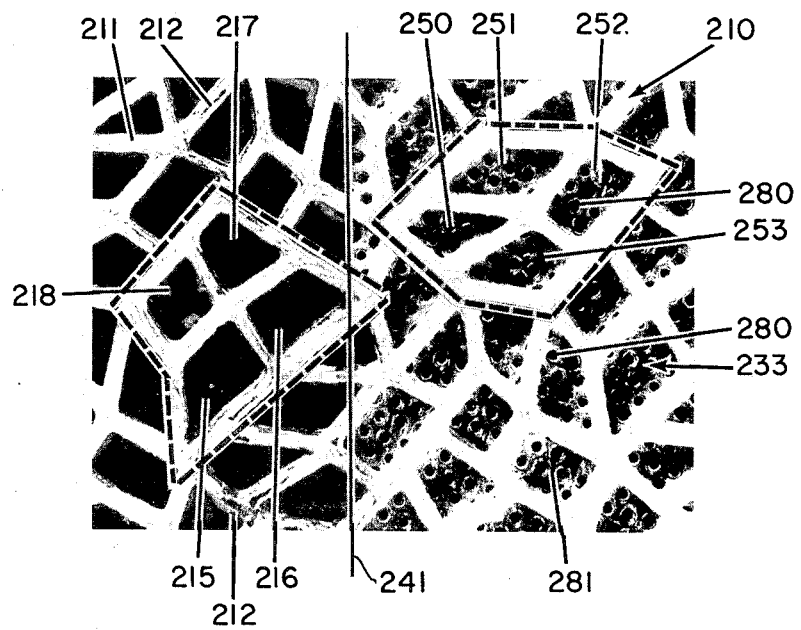
FIG. 8 is a plan view photograph enlarged approximately twelve times actual size of a preferred laminate forming structure generally similar to that illustrated in FIG. 2, but incorporating the present invention to provide selective aperturing of a plastic film subjected to a fluid pressure differential while in contact therewith.

FIG. 8 is a plan view photograph enlarged approximately twelve times actual size of a preferred laminate film forming structure 210 of the present invention. The laminate film forming structure 210 is in most respects similar to the laminate film forming structure 10 illustrated in FIG. 2, i.e., a random pattern of capillary networks, each defined by a multiplicity of interconnected fiber-like elements. It was created by superposing a stack of laminar sheets upon one another with their aperture patterns in vertical alignment, the assembled stack being bonded in accordance with the teachings of the aforementioned application of Radel et al. to form an integral laminate structure. When viewed from the plan, the fully apertured portion of the laminate film forming structure 210 to the left of dividing line 241 appears essentially the same as the fully apertured laminate film forming structure 10 illustrated in FIG. 2. A random pattern of capillary networks comprising apertures, e.g., apertures 215 through 218, propagates all the way from the uppermost surface 211 to the lowermost surface of the laminate structure 210. In this regard, note the pattern similarity to apertures 15 through 18, respectively, in laminate forming structure 10 shown in FIG. 2.

The uppermost lamina of structure 210 is provided with a multiplicity of grooves 212 generally similar to the grooves 12 in film forming structure 10 to provide desired surface roughness. That portion of the structure 210 to the left of dividing line 241 corresponds to that portion of the plastic film to be apertured. Conversely, that portion of the forming structure 210 to right of dividing line 241 is provided with a perforate but unetched lamina 233 intermediate the uppermost and lowermost lamina. This provides a supporting surface for those portions of the plastic film to be debossed but not apertured.

Figure 9:
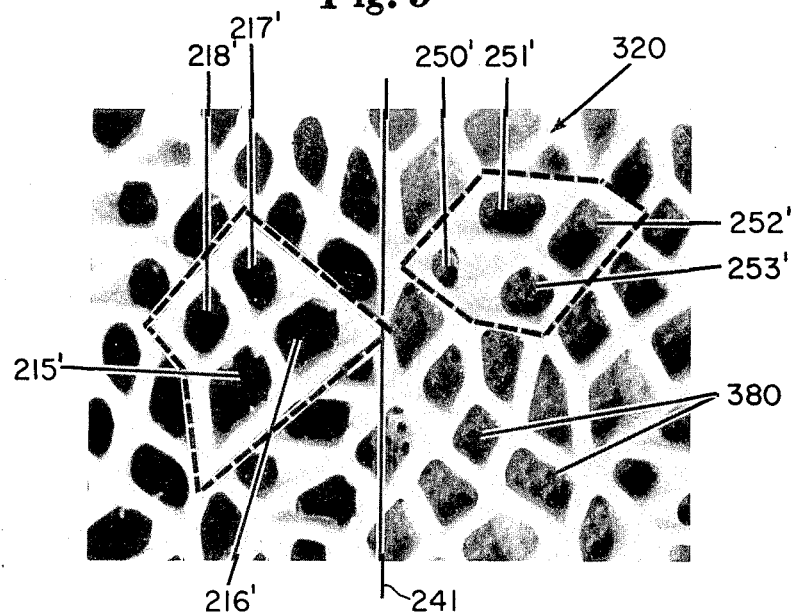
FIG. 9 is a plan view photograph enlarged approximately twelve times actual size of a plastic film which has been caused to conform to a laminate forming structure of the type generally illustrated in FIG. 8 and selectively apertured in those areas where the initially perforate lamina has been apertured.

The regulated pattern of perforations 280 in the unetched portion 281 of lamina 233 permit the application of uniform fluid pressure, preferably vacuum, to the lowermost surface of the heated plastic film brought into contact with the forming structure 210, thus providing effective debossing of the film in those areas where aperturing is not desired. Those portions of the film which are unsupported by the perforate portion 281 of selectively apertured lamina 233, i.e., those portions to the left of dividing line 241, are not only debossed, but apertured as well. As shown in FIG. 9, application of a uniform level of vacuum to the lowermost surface of forming structure 210 will produce a selectively apertured plastic film 320 exhibiting a substantially uniform three-dimensional texture across its entire surface.

In a particularly preferred embodiment of the present invention, the laminae used to construct laminate forming structure 210, including selectively apertured lamina 233, are created by means of highly versatile photoetching techniques. These techniques make it feasible to precisely control the areas to be apertured and the areas to be debossed but not apertured in the resultant plastic film. Depending upon the size and frequency of the debossments, it may also be feasible to create laminae suitable for use in forming structures of the present invention by more conventional techniques, e.g., punching, stamping, noncontact machining, etc.

Figure 10:
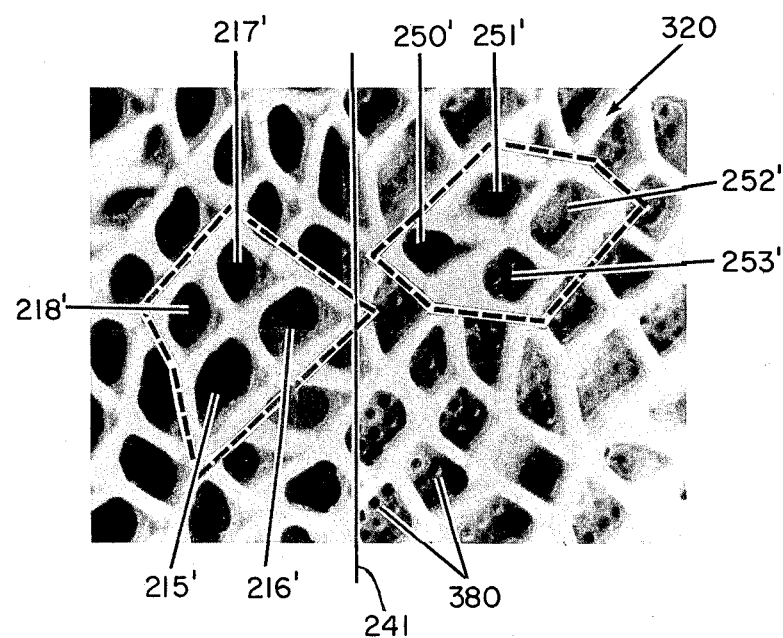
FIG. 10 is a plan view photograph enlarged approximately twelve times actual size of a selectively apertured plastic film of the type shown in FIG. 9 after removal from a laminate forming structure of the type shown generally in FIG. 8.

FIG. 9 is a plan view photograph enlarged approximately twelve times of a 1.4 mil thick polyethylene plastic film 320 which has been debossed and selectively apertured in accordance with the present invention on a laminate film forming structure of the type generally illustrated in FIG. 8. Those portions of the film 320 to the left of dividing line 241, which coincides with the edge of perforate lamina 233, exhibit apertures, i.e., 215', 216', 217', and 218' corresponding to apertures 215, 216, 217 and 218, respectively, in forming structure 210. Those portions of the film 320 to the right of dividing line 241 exhibit debossed, but non-apertured areas, i.e., 250', 251', 252' and 253' corresponding to apertures 250, 251, 252 and 253, respectively, in forming structure 210. The film 320 shown in FIG. 9 is still in contact with a forming surface 210 of the type generally shown in FIG. 8. The majority of dark spots 380 in those portions of the film to the right of dividing line 241 are not perforations, but are due partially to background visibility of the perforations 280 in selectively apertured lamina 233 and partially to a degree of film deformation which took place during the forming operation. This is somewhat more apparent from FIG. 10, wherein a selectively apertured film 320 of the type shown in FIG. 9 has been removed from the forming structure 210.

Because the photoetching technique utilized to create preferred forming structures of the present invention can be practiced on an extremely fine scale, it is difficult to discern any difference in texture and appearance between the apertured and the non-apertured areas of the film 320 when viewed at actual size by the naked human eye. This difference becomes even less apparent when the selectively apertured film is utilized in applications such as a diaper or a sanitary napkin top sheet, wherein the absorbent material located beneath the apertured portion of the plastic film 320 exhibits a color generally similar to that of the film.

Figure 11:
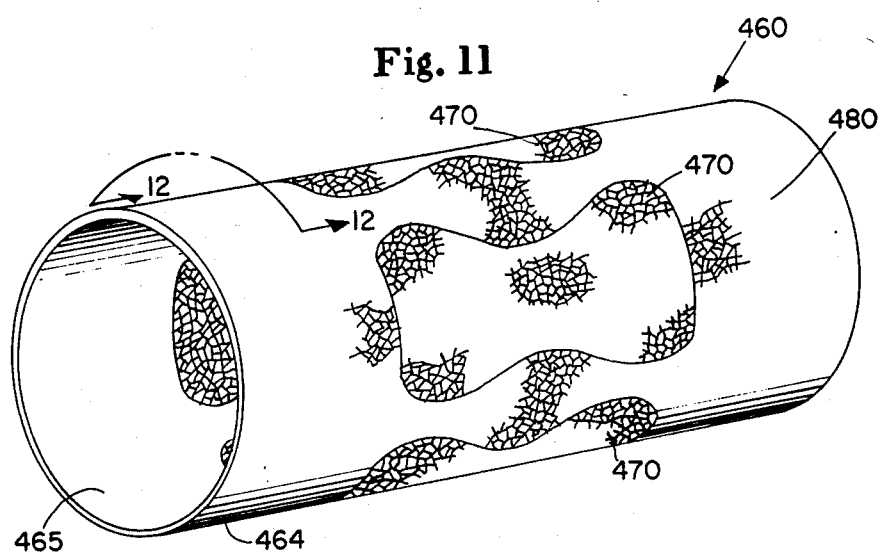
FIG. 11 is a perspective view of a tubular member formed by rolling a planar laminate structure of the type generally illustrated in FIG. 8 to the desired radius of curvature and joining the free ends thereof to one another.

In a particularly preferred embodiment, selectively apertured, laminate forming structures of the present invention are rolled by conventional techniques into tubular forming members 460, as generally illustrated in FIG. 11. Contrary to expectations, it has been determined that rolling the planar laminate structure, which is preferably constructed generally in accordance with the teachings of the aforementioned co-pending commonly assigned patent application of Radel et al., into a tubular shape does not tend to cause delamination of the structure, provided the furnace brazing operation utilized to join the lamina has been properly carried out. Where extremely intricate patterns are present in the laminate structure, it has been learned that placing a thin sheet of urethane on opposite sides of the laminate structure as it is passed through the metal rolls will minimize the chance of injury to the fine pattern while rolling the member into the desired tubular shape.

The outermost surface 464 of the tubular forming member 460 is utilized to deboss and selectively aperture plastic film webs brought in contact therewith while the innermost surface 465 of the tubular member generally does not contact the plastic web during the forming operation. As shown in FIG. 11, those portions of the plastic web to be apertured contact the tubular member at areas 470 where the selectively apertured lamina contains a pattern of apertures coinciding with that of the other laminae in the forming structure, while the remaining portions of the laminate forming structure represent the areas where the selectively apertured lamina does not contain a pattern of apertures coinciding with the pattern of apertures in the other laminae. Thus, while the overall surface of the film will be caused to exhibit a substantially uniform three-dimensional texture and appearance, only those portions 470 will be apertured.

Figure 14:
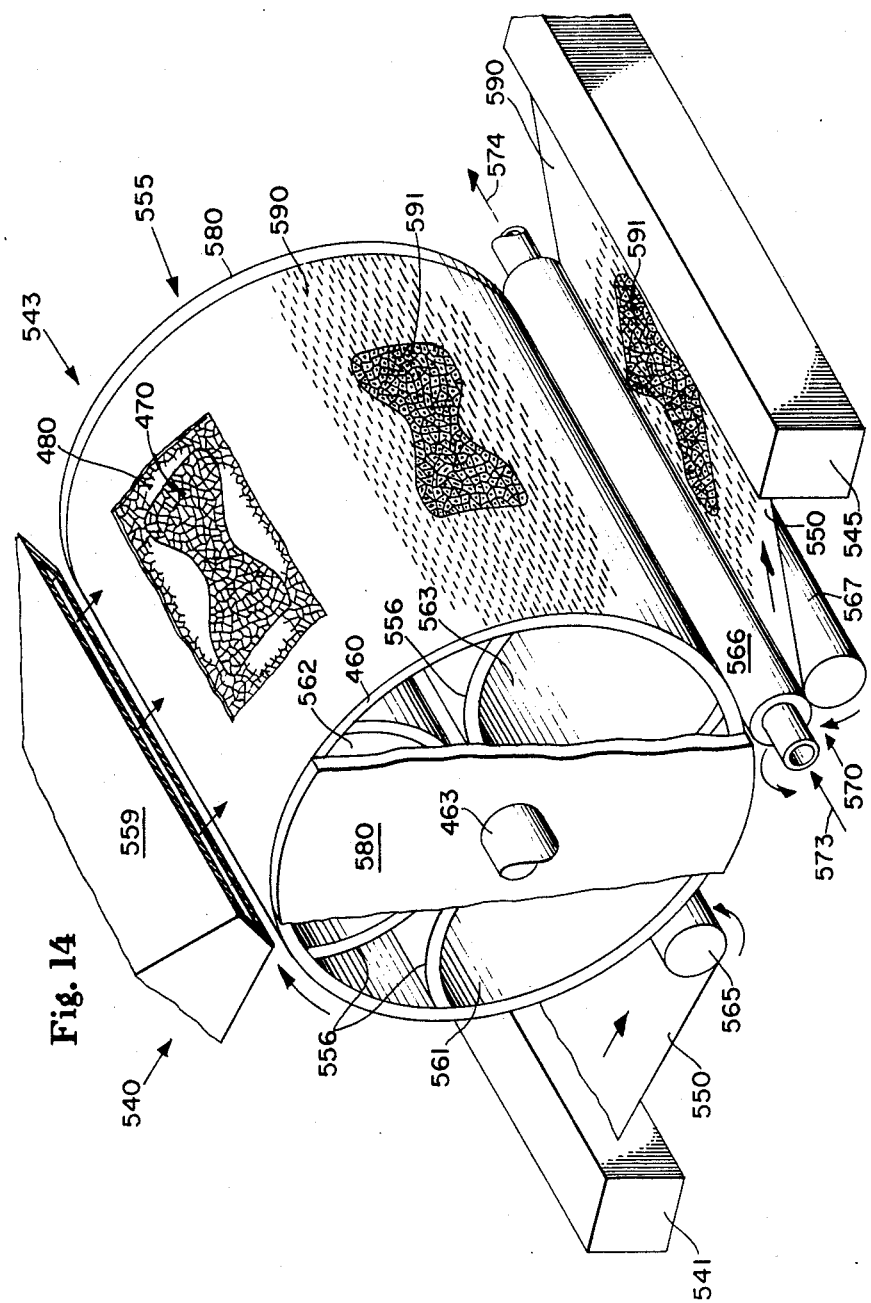
FIG. 14 is a simplified schematic illustration of a method and apparatus for debossing and selectively aperturing a plastic film generally in accordance with the present invention.

The tubular member 460 generally shown in FIG. 11 may, in a preferred embodiment of the present invention, be employed as the forming surface on debossing-/aperturing cylinder 555 in a process of the type generally illustrated in FIG. 14, said process being described in detail in U.S. Pat. No. 4,151,240 issued to Lucas et al. on Apr. 24, 1979, said patent being incorporated herein by reference.

Laminate fabricating techniques provide the ability to join the free ends of a single forming section to one another or the ability to join one forming section to another forming section of similar pattern with substantial continuity in the selectively apertured three-dimensional pattern throughout the structure in the area of joinder. The laminating technique may also be employed to advantage to join a multiplicity of small forming sections to one another where, for one reason or another, it is impractical to integrally form the individual lamina in large enough size.

Figure 12:
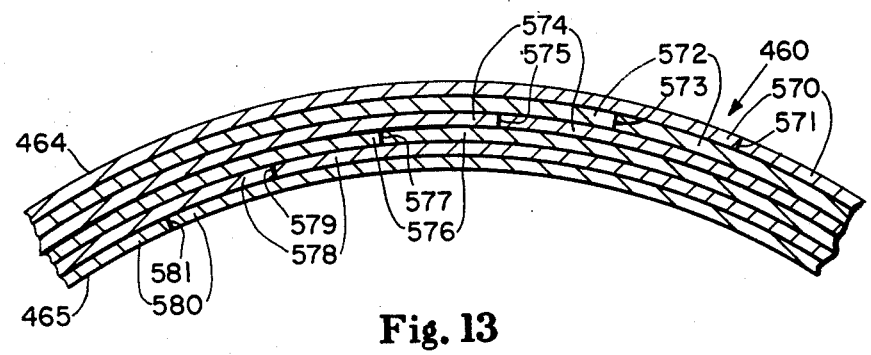
FIG. 12 is an enlarged, simplified cross-sectional view taken along section line 12—12 of FIG. 11 illustrating a preferred lap seaming technique for joining the free ends of the laminate structure to one another without substantially disrupting the three-dimensional, selectively apertured pattern of the laminate structure in the area of joinder.

FIG. 12, which is a simplified cross-sectional view taken along section line 12—12 of FIG. 11, illustrates one preferred manner of joining the free ends of tubular member 460 to one another to provide an integral tubular structure exhibiting substantially no discontinuity in the selectively apertured, three-dimensional pattern in the area of joinder. In the embodiment shown in FIG. 12, a lap seam is created by allowing each free end of the planar photoetched laminate structure from which tubular member 460 is formed to project in a manner resembling a series of parallel stairsteps. The stairstep edges may be provided by properly stacking the laminae prior to bonding, or by non-contact machining techniques after the structure has been bonded. Since the pattern exhibited by each photoetched lamina is precisely regulated and highly repeatable, rolling the planar laminate structure into a tubular shape causes the mating free ends to align with one another in stairstep fashion as illustrated in FIG. 12. Thus, if the slight differences in radius of curvature for each successive lamina in the stack are ignored, corresponding parts of the pattern employed in lamina 570 mate with one another at 571; corresponding parts of the pattern employed in lamina 572 mate with one another at 573; corresponding parts of the pattern employed in lamina 574 mate with one another at 575; corresponding parts of the pattern employed in lamina 576 mate with one another at 577; corresponding parts of the pattern employed in lamina 578 mate with one another at 579; and corresponding parts of the pattern employed in lamina 580 mate with one another at 581. As is apparent from FIG. 12, no individual lamina seam is radially aligned with another, yet the selectively apertured three-dimensional pattern of the tubular member 460 existing between the outermost surface 464 and the innermost surface 465 is substantially identical at any point along the periphery of the tubular member, including the area of joinder. Furthermore, the resultant seam has much greater strength than a radially aligned butt joint due to the reinforcing effect of one lamina on its adjacent lamina. Joinder of the lap seam shown in FIG. 12 is preferably carried out by applying a low melting point bonding alloy to the area of joinder utilizing either a torch or a brazing furnace, as generally described in the aforementioned copending commonly assigned patent application of Radel et al. The low melting point metal bonding alloy bonds itself to the laminate structure without creating a substantial discontinuity in the area of joinder while at a temperature which is sufficiently low that it does not adversely affect the copper bonding within the structure per se. Alternatively, the joint could be furnace brazed in the same manner the laminate structure is bonded together, provided the areas outside the joint are protected against excessive heat.

Figure 13:
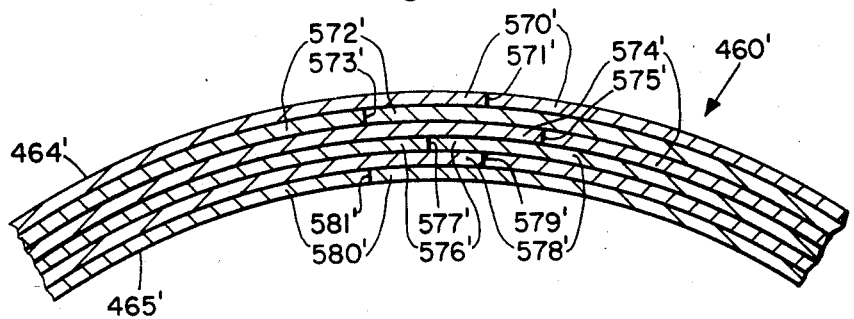
FIG. 13 is a view similar to that of FIG. 12 illustrating yet another lap seaming technique which can be used to join the free ends of the laminate structure to one another without substantially disrupting the three-dimensional, selectively apertured pattern in the area of joinder.

FIG. 13 is a view similar to that of FIG. 12, but illustrating yet another lap seaming technique which may, if desired, be employed to join the free ends of laminar structures of the present invention to one another. Care must, however, be exercised with the construction generally illustrated in FIG. 13 to prevent non-adjacent lamina from bonding to one another at their free edges during the furnace brazing operation while the laminate structure is in planar condition. One method of avoiding such problems is to temporarily insert thin ceramic paper intermediate the non-adjacent lamina at the exposed edges during the planar phase of the furnace brazing operation.

In the tubular embodiment of FIG. 13, the free ends of tubular element 460' are interleaved with one another such that, if the slight differences in radius of curvature for each successive lamina in the stack are ignored, corresponding portions of the pattern contained in lamina 570' are mated to one another at 571'; corresponding portions of the pattern contained in lamina 572' are mated to one another at 573'; corresponding portions of the pattern contained in lamina 574' are mated to one another at 575'; corresponding portions of the pattern contained in lamina 576' are mated to one another at 577'; corresponding portions of the pattern contained in lamina 578' are mated to one another at 579'; and corresponding portions of the pattern contained in lamina 580' are mated to one another at 581'. Thus, no lamina seam is in radial alignment with an adjacent lamina seam, yet the three-dimensional, selectively apertured pattern existing between the outermost surface 464' and the innermost surface 565' of the tubular member 460' is substantially continuous at any point along the periphery of the drum, including the area of joinder of the free ends.

Thus, a cylindrical forming structure exhibiting substantial continuity of pattern along its entire periphery is provided. This permits continuous formation of a plastic film web exhibiting the desired selectively apertured, three-dimensional pattern without a seam discontinuity of the type typically present in prior art forming structures. As will be readily apparent to those skilled in the art, the present invention may be applied to great advantage to produce selectively apertured plastic webs exhibiting nearly any three-dimensional pattern, characteristic, property or appearance desired.

As will be appreciated by those skilled in the art, the fabrication and bonding techniques described above define particularly preferred embodiments of the present invention. Depending upon where the selectively apertured lamina is positioned in relation to other laminae in the stack, it may be feasible to leave those laminae located intermediate the selectively apertured lamina and the outermost surface of the tubular member unbonded to said selectively apertured lamina. In such an arrangement, changing said outermost laminae as an integral unit would readily permit changing the three-dimensional pattern of embossments to be imparted to the web while maintaining the same line of demarcation between the apertured and non-apertured areas.

The inherent flexibility of photographic techniques makes it feasible to create nearly any structure desired by designing the particular characteristics sought into each layer and thereafter photographically reducing or enlarging the size of the pattern to whatever scale is desired in the photoetched lamina. In other embodiments of the present invention photographs of existing structures exhibiting desirable characteristics could be utilized to form one or more of the photoetched lamina. A composite stack comprised of individual lamina of varying patterns and including at least one selectively apertured lamina of the present invention may thereafter be assembled generally in accordance with the teachings of the aforementioned application of Radel et al. to produce a laminate forming structure exhibiting characteristics and properties not achievable by prior art means.

A particularly preferred continuous process for forming debossed, selectively apertured plastic films which may employ a tubular laminate forming structure of the type generally shown in FIGS. 12 and 13 is schematically illustrated in FIG. 14. This process is generally described in U.S. Pat. No. 4,151,240 issued to Lucas et al. on Apr. 24, 1979 and incorporated herein by reference. A particularly preferred apparatus 540 of the type disclosed in said patent is schematically shown in FIG. 14. It includes constant tension film supply means 541, debossing and aperturing means 543, and constant tension film forwarding and winding means 545. The frame, bearings, supports and the like which must necessarily be provided with respect to the functional members of apparatus 540 are not shown or described in detail in order to simplify and more clearly disclose the present invention, it being understood that such details would be obvious to persons of ordinary skill in the film converting machinery art.

Briefly, apparatus 540, FIG. 14, comprises means for continuously converting a ribbon of thermoplastic film 550 into a debossed and selectively apertured film by directing hot air jets against one surface of the film while applying vacuum adjacent the opposite surface of the film, and while maintaining sufficient control of the film 550 to substantially obviate wrinkling and/or macroscopically distending the film. Thus, as will be more fully described hereinafter, apparatus 540 comprises means for maintaining constant machine direction tension in the film both upstream and downstream of a zone where the temperature is greater than the softening temperature of the film, which is typically its thermoplastic temperature, but in which zone there is substantially zero machine direction and substantially zero cross-machine direction tension tending to macroscopically distend the film. The tension is required to control and smooth a running ribbon of thermoplastic film; the zero tension zone results from the film in the zone being at a temperature sufficiently high to soften the film and thereby enable debossing and, where desired, aperturing thereof via the application of vacuum to the interior surface of the laminate tubular member. FIG. 14 has been greatly enlarged and partially broken away to enable visually perceiving the nature of the difference between the debossed but non-apertured portions 590 and the debossed and apertured portions 591 of the film 550, as more fully described hereinafter. The debossed but non-apertured portions 590 of the film 550 are formed by those portions of tubular forming structure 460 which correspond to the non-coinciding portions of the selectively apertured lamina, while the debossed and apertured portions 591 of the film correspond to those portions 470 of the tubular forming structure which contain the coinciding portion of the selectively apertured lamina.

As can be seen in FIG. 14, the debossing and aperturing means 543 includes a rotatably mounted cylinder 555 for debossing and selectively aperturing plastic films coming in contact therewith, said cylinder having closed ends 580, a nonrotating triplex vacuum manifold assembly 556 and hot air jet means 559. The triplex vacuum manifold assembly 556 comprises three manifolds designated 561, 562, and 563. Also shown in FIG. 14 is a freely rotatable lead-on idler roll 565, a power rotated lead-off/chill roll 566, and a soft-face (e.g., low density neoprene) roll 567 which is driven with the chill roll. Briefly, by providing means (not shown) for independently controlling the level of vacuum in the three vacuum manifolds, a thermoplastic ribbon of film running circumferentially about a portion of the debossing-aperturing cylinder 555 is sequentially subjected to a first level of vacuum by manifold 561, a second level of vacuum by manifold 562, and a third level of vacuum by manifold 563. As will be described more fully hereinafter, the vacuum applied to the film by manifold 561 enables maintaining upstream tension in the film, vacuum applied by manifold 562 enables debossing and selectively aperturing the film when hot air is directed radially inwardly against the film, and vacuum applied by manifold 563 enables cooling the film to below its softening temperature and enables establishing downstream tension therein. If desired, the film-contacting surface of the debossing-aperturing cylinder 555 may be preheated prior to reaching vacuum manifold 562 by means well known in the art (and therefore not shown) to facilitate better conformance of plastic films comprised of flow-resistant polymers during the debossing and selective aperturing operation. The nip 570 intermediate chill roll 566 and the softface roll 567 is only nominally loaded because high pressure would iron-out the three-dimensional debossments which are formed in the film in the aforementioned manner. However, even nominal pressure in nip 570 helps the vacuum applied by manifold 563 to isolate downstream tension (i.e., roll winding tension) from the debossing-aperturing portion of the debossing-aperturing cylinder 555, and enables the nip 570 to peel the debossed and selectively apertured film from the debossing-aperturing cylinder 555. Moreover, while vacuum drawn ambient air passing through the apertured portions 591 of the film into manifold 563 will normally aid in cooling the film to below its softening temperature, the passage of coolant through the chill roll 566 as indicated by arrows 573, 574 in FIG. 14 will enable cooling of the non-apertured portions 590 of the film 550.

To summarize, the first vacuum manifold 561, and the third vacuum manifold 563 located within the debossing-aperturing cylinder 555 enable maintaining substantially constant upstream and downstream tension respectively in a running ribbon of film while the intermediate portion of the film adjacent the second vacuum manifold 562 within the debossing-aperturing cylinder 555 is subjected to tension vitiating heat and vacuum to effect debossing and selective aperturing of the film.

Referring again to FIG. 14, the constant tension film supply means 541 and the constant tension film forwarding and winding means 545 may, if desired, be substantially identical to and function substantially identically to the corresponding portions of the apparatus shown and described in U.S. Pat. No. 3,674,221 issued to Riemersma on July 4, 1972 and which is hereby incorporated herein by reference. The debossing and selective aperturing means 543 comprises the rotatably mounted debossing-aperturing cylinder 555, means (not shown) for rotating the cylinder 555 at a controlled peripheral velocity, the non-rotating triplex vacuum manifold assembly 556 inside the debossing-aperturing cylinder 555, means (not shown) for applying controlled levels of vacuum inside the three vacuum manifolds 561, 562 and 563 comprising the triplex manifold assembly 556, and hot air jet means 559.

The debossing-selective aperturing cylinder 555 may be constructed by generally following the teachings of the aforementioned commonly assigned patent of Lucas et al., but substituting a tubular laminate forming structure 460 of the type generally shown in FIG. 11 for the perforated tubular forming surface disclosed therein. Ends 580 are secured in sealed relation to the lateral edges of the forming structure and the entire cylinder 555 is supported by means of a shaft 463 passing through its center and secured to ends 580.

While particular embodiments of the present invention have been illustrated and described, it will be obvious to those skilled in the art that various changes and modifications can be made without departing from the spirit and scope of the invention, and it is intended to cover in the appended claims all such modifications that are within the scope of this invention.

What is claimed is:

1. A continuous method of forming a plastic web exhibiting a substantially continuous three-dimensional pattern of debossments, a predetermined portion of said debossments being apertured at preselected points along the surface of said plastic web, said method comprising the steps of:

(a) continuously bringing said plastic web in contact relation with a tubular-shaped laminate forming structure exhibiting a substantially continuous first pattern of apertures corresponding to said debossments and extending from the outermost to the innermost surface of said tubular-shaped structure, those apertures corresponding to the non-apertured debossments in said web having a perforate support member exhibiting a second pattern of apertures smaler in size than the apertures in said first pattern located interiorly of the outermost surface of said laminate structure, each of the apertures in said second pattern being sufficiently small in size to substantially prevent rupture of said web in those areas coinciding with said apetures in said second pattern when said web is subjected to a fluid pressure differential sufficient to aperture those debossments which do not coincide with said perforate support member;

(b) heating the portion of said web in contact with said forming structure above its softening temperature;

(c) applying a substantially uniform fluid pressure differential to said heated plastic web in those areas to be debossed but not apertured and in those areas to be debossed and apertured and said first and second patterns of apertures in said tubular-shaped forming structure while said web is in contact with said forming structure, whereby said web is debossed in the image of said laminate forming structure yet substantially prevented from being apertured where said perforate support member contact said web due to the support afforded said web by said perforate support member and debossed and apertured in those portions of said forming structure where said perforate support member does not contact said web;

(d) cooling said debossed and selectively apertured web below its softening temperature; and (e) removing said debossed and selectively apertured web from said forming structure.

2. The method of claim 1, wherein said tubular-shaped perforate laminate film forming structure is preheated prior to bringing said plastic web into contacting relation therewith to facilitate better overall conformance of said web to said forming structure.

3. The method of claim 1, wherein said fluid pressure differential applied to said web in those areas to be debossed but not apertured and in those areas to be debossed and apertured and said first and second patterns of apertures in said tubular-shaped forming structure comprises suction applied to the interior of said tubular-shaped forming structure.

4. The method of claim 1, wherein said web is heated by directing a curtain of hot air against said plastic web while said web is in contact with said forming structure.

5. A continuous method of forming a plastic web exhibiting a substantially continuous three-dimensional pattern of debossments, a predetermined portion of said debossments being apertured at preselected points along the surface of said plastic web, said method comprising the steps of:

(a) continuously extruding a melt of plastic resin onto the periphery of a tubular-shaped laminate forming structure exhibiting a substantially continuous first pattern of apertures corresponding to said debossments and extending from the outermost to the innermost surface of said tubular-shaped structure, those apertures corresponding to the non-apertured debossments in said web having a perforate support member exhibiting a second pattern of apertures smaller in size than the apertures in said first pattern located interiorly of the outermost surface of said laminate structure, each of the apertures in said second pattern being sufficiently small in size to substantially prevent rupture of said web in those areas coinciding with said apertures in said second pattern when said web is subjected to a fluid pressure differential sufficient to aperture those debossments which do not coincide with said perforate support member;

(b) maintaining the portion of said plastic melt in contact with said forming structure above its softening temperature;

(c) applying a substantially uniform fluid pressure differential to said heated plastic melt in those areas to be debossed but not apertured and in those areas to be debossed and apertured and said first and second patterns of apertures in said tubular-shaped forming structure while said melt is in contact with said forming structure, whereby said web is debossed in the image of said lamiante forming structure yet substantially prevented from being aerptured where said perforate support member contacts said melt due to the support afforded said web by said perforate support member and debossed and apertured in those portions of said forming structure where said perforate support member does not contact said melt;

(d) cooling said debossed and selectively apertured melt below its softening temperature to form a web; and (e) removing said debossed and selectively apertured web from said forming structure.

6. The method of claim 5, wherein said tubular-shaped perforate laminate film forming structure is preheated prior to bringing said plastic melt into contacting relation therewith to facilitate better overall conformance of said web to said forming structure.

7. The method of claim 5, wherein said fluid pressure differential applied to said melt in those areas to be debossed but not apertured and in those areas to be debossed and apertured and said first and second patterns of apetures in said tubular-shaped forming structure comprises suction applied to the interior of said tubular-shaped forming structure.

8. The method of claim 5, wherein said melt is maintained above its softening temperature by directing a curtain of hot air against said plastic melt while said melt is in contact with said forming structure.

* * * * *

UNITED STATES PATENT AND TRADEMARK OFFICE
CERTIFICATE OF CORRECTION

PATENT NO. : 4,747,991
DATED : May 31, 1988
INVENTOR(S) : Delmar J. Bishop

It is certified that error appears in the above-identified patent and that said Letters Patent is hereby corrected as shown below:

Column 3, line 21, after "4,342,314" insert -- issued --.

Column 4, line 33, "aperture" should read -- apertures --.

Column 13, line 6, insert "." after "Z".

Column 19, line 63, "softface" should read -- soft-face --.

Column 21, line 3, "smaler" should read -- smaller --.

Column 22, line 50, "apetures" should read -- apertures --.

Signed and Sealed this

Twenty-fifth Day of October, 1988

Attest:

DONALD J. QUIGG

Attesting Officer

Commissioner of Patents and Trademarks